US00PP21730P2

(12) United States Plant Patent
Chodyla

(10) Patent No.: US PP21,730 P2
(45) Date of Patent: Feb. 22, 2011

(54) ***HOSTA* PLANT NAMED 'HOST SUN 08'**

(50) Latin Name: *Hosta hybrida*
Varietal Denomination: Host Sun 08

(76) Inventor: Bernard Chodyla, 7756 Preservation Rd., Tallahassee, FL (US) 32312

( * ) Notice: Subject to any disclaimer, the term of this patent is extended or adjusted under 35 U.S.C. 154(b) by 0 days.

(21) Appl. No.: 12/460,184

(22) Filed: Jul. 15, 2009

(51) Int. Cl.
*A01H 5/00* (2006.01)

(52) U.S. Cl. ..... Plt./353

(58) Field of Classification Search ..... Plt./353
See application file for complete search history.

*Primary Examiner*—Kent L Bell
(74) *Attorney, Agent, or Firm*—Mark Bourgeois

(57) ABSTRACT

A new and distinct *Hosta* plant cultivar is disclosed, characterized by a better performance in the sun than other *Hosta* varieties known to the inventor; large, oval-shaped leaves; very low cold requirements and bright green leaves with wide, creamy yellow-white margins.

1 Drawing Sheet

Latin name of the genus and species: *Hosta hybrida.*
Variety denomination: 'HOST SUN 08'.

BACKGROUND OF THE INVENTION

The new cultivar 'HOST SUN 08' is a naturally occurring chimeral mutation of the variety 'So Sweet' (unpatented in the United States). The new cultivar was discovered and selected by Bernard Chodyla in April 2004 in Crawfordville, Fla.

Asexual reproduction of the new cultivar 'HOST SUN 08' by division and tissue culture was performed in Crawfordville, Fla. and Oxnard, Calif., and has shown that the unique features of this new cultivar are stable and reproduced true to type on successive generations.

SUMMARY OF THE INVENTION

The cultivar 'HOST SUN 08' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'HOST SUN 08'. These characteristics in combination distinguish 'HOST SUN 08' as a new and distinct *Hosta* cultivar:

1. Performs better in the sun than other *Hosta* varieties known to the inventor;
2. Very low cold requirements;
3. Bright green leaves with wide, creamy yellow-white margins.

Plants of the new cultivar 'HOST SUN 08' are similar to plants of the parent variety, 'So Sweet' in most horticultural characteristics, however 'HOST SUN 08' is slightly shorter than the parent variety. Also, the leaves of 'HOST SUN 08' have broader white-colored edges and a lighter green color than the leaves of the parent variety. Finally, 'HOST SUN 08' performs better in the full sun and has a lower cold requirement.

In comparison to the commercially available variety 'Forest Fire' (U.S. Plant Pat. No. 17,644), 'HOST SUN 08' is taller and has a wider plant spread. Additionally, the foliage of the new variety 'HOST SUN 08' is a much brighter green than the foliage of 'Forest Fire'. Further, the markings on the foliage of the new variety 'HOST SUN 08' are different in shape than 'Forest Fire.' Finally, 'HOST SUN 08' performs better in the sun and has a lower cold requirement.

BRIEF DESCRIPTION OF THE PHOTOGRAPH

The accompanying photograph illustrates in full color a typical plant of 'HOST SUN 08' grown in an outdoor garden. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'HOST SUN 08' plants grown in Oxnard, Ventura County, Calif., during the months of December through February. The growing temperature ranged from 12° C. to 15° C. at night to 12° C. to 20° C. during the day. Measurements and numerical values represent averages of typical *Hosta* plants.

Botanical classification: *Hosta* hybrid cultivar 'HOST SUN 08'.

Commercial classification: *Hosta.*

PROPAGATION

Method: By sterile laboratory tissue culture division and garden division.

Time to initiate roots from both division and tissue culture: Two to three weeks.

Rooting habit: Normal, fleshy, lightly branching.

PLANT

Form: Annual potted or garden plant.

Growth habit: Mounded plant form with broadly spreading foliage.

Branching habit: Very well branched plant with multiple glossy leaves.

Crop time: Under normal summer growing conditions about 16 weeks to finish in a one-liter container.
Vigor: Good to high; it takes about 12 month to produce fully grown plants from tissue culture micros.
Longevity: 'HOST SUN 08' is the last variety known to the inventor to go dormant. In zones 10a and 10b it will stay green year around, plants will bloom in April if planted in the fall. In other zones where subject to winter dormancy, 'HOST SUN 08' will bloom in July and August.
Plant height: About 60 cm.
Plant diameter: About 52 cm.

FOLIAGE

Arrangement: Opposite; simple.
Length: About 18 cm.
Width: About 11 cm.
Shape: Oval.
Apex: Broadly acuminate.
Base: Rounded.
Margin: Crenate.
Texture:
*Upper surface.*—Lightly pubescent.
*Lower surface.*—Lightly pubescent.
Venation pattern: Pinnate; netted.
Color:
*Developing foliage on the upper surface.*—Towards the margins: Near Greyed-Yellow 160A. Towards the center: Near Green 143B. Center: Near Green 137A. Towards the base: Green 137A. Venation: Near Green 143A.
*Developing foliage on the lower surface.*—Towards the margins: Near Greyed-Yellow 160A. Towards the center: Near Green 143C. Center: Near Green 137A. Towards the base: Near Green 137A. Venation: Near Green 143A.
*Fully expanded foliage on the upper surface.*—Towards the margins: Near Yellow-White 158C. Towards the center: Near Green 143C. Center: Near Green 143C. Towards the base: Near Green 137B. Venation: Near Green 143A.
*Fully expanded foliage on the lower surface.*—Towards the margins: Near Yellow-White 158C. Towards the center: Near Green 143C. Center: Near Green 143C. Towards the base: Near Green 137B. Venation: Near Green 143A.
Petiole length: About 26 cm.
Petiole diameter: About 1.1 cm.
Petiole color:
*Towards the apex.*—Near Green 137D.
*Towards the base.*—Near Green 137D.

FLOWER

Inflorescence type: Terminal racemes with flowers facing outward.
Inflorescence longevity: About 2 weeks.
Flower shape: Tubular.
Flower number: About 15-20.
Flower fragrance: None detected.
Flower bud shape: Spatulate.
Flower bud size:
*Length.*—About 12.7 cm.
*Diameter.*—About 3.8 cm.
Flower bud color: Near White 155D.
Flower size:
*Length.*—About 21.6 cm.
*Diameter.*—About 12.7 cm at its widest point, tube portion is about 2 cm.
Flower color: Near White 155D.
Pedicels:
*Length.*—About 3 mm.
*Diameter.*—About 2 mm.
*Color.*—Near White 155B.
Perianth: Comprised of 6 tepals, 3 interior and 3 exterior, fused in tube region.
Tepal shape: Oblanceolate.
Tepal size:
*Length.*—About 20 cm.
*Diameter.*—About 3 cm.
Tepal color: Near White 155B.
Tepal texture: Glabrous.
Bracts: 1 per flower.
Bract shape: Ovate.
Bract texture: Glabrous.
Bract color: Near Green 143C with near White 155D at margins.
Bract length: About 4 cm.
Bract width: About 2.1 cm.

REPRODUCTIVE ORGANS

Gynoecium:
*Pistil.*—1.
*Style length.*—About 22 cm.
*Style width.*—About 3 mm.
*Style color.*—Near White 155B.
*Stigma color.*—Near Yellow 4D.
*Ovary shape.*—Oblong.
*Ovary length.*—About 7 mm.
*Ovary width.*—About 4 mm.
*Ovary color.*—Near Yellow-White 158B.
Androecium:
*Stamens.*—6.
*Filament color.*—Near White 155B.
*Filament length.*—About 20 cm.
*Filament diameter.*—About 2 mm.
*Anther length.*—About 1 cm.
*Anther width.*—About 1 cm.
*Anther color.*—Near Greyed-Yellow 162B.
*Pollen.*—Pollen is sparse and near Yellow 6C.

OTHER CHARACTERISTICS

Disease resistance: Very resistant to pest and disease.
Drought tolerance/cold tolerance: 'HOST SUN 08' performs best in the full sun and hot, humid conditions of the Southeast. Plants will express its full white variegation in full sun only. 'HOST SUN 08' has very low cold requirements comparing to other *Hosta* varieties known to the inventor. It will stay vegetative under short days during winter months in South Florida. It has a very good drought tolerance.
Fruit/seed production: Commercially, this plant is not used or observed in a stage where seeds would be produced. Therefore, seed production has not been observed.

What is claimed is:

1. A new and distinct cultivar of *Hosta* plant named 'HOST SUN 08' as herein illustrated and described.

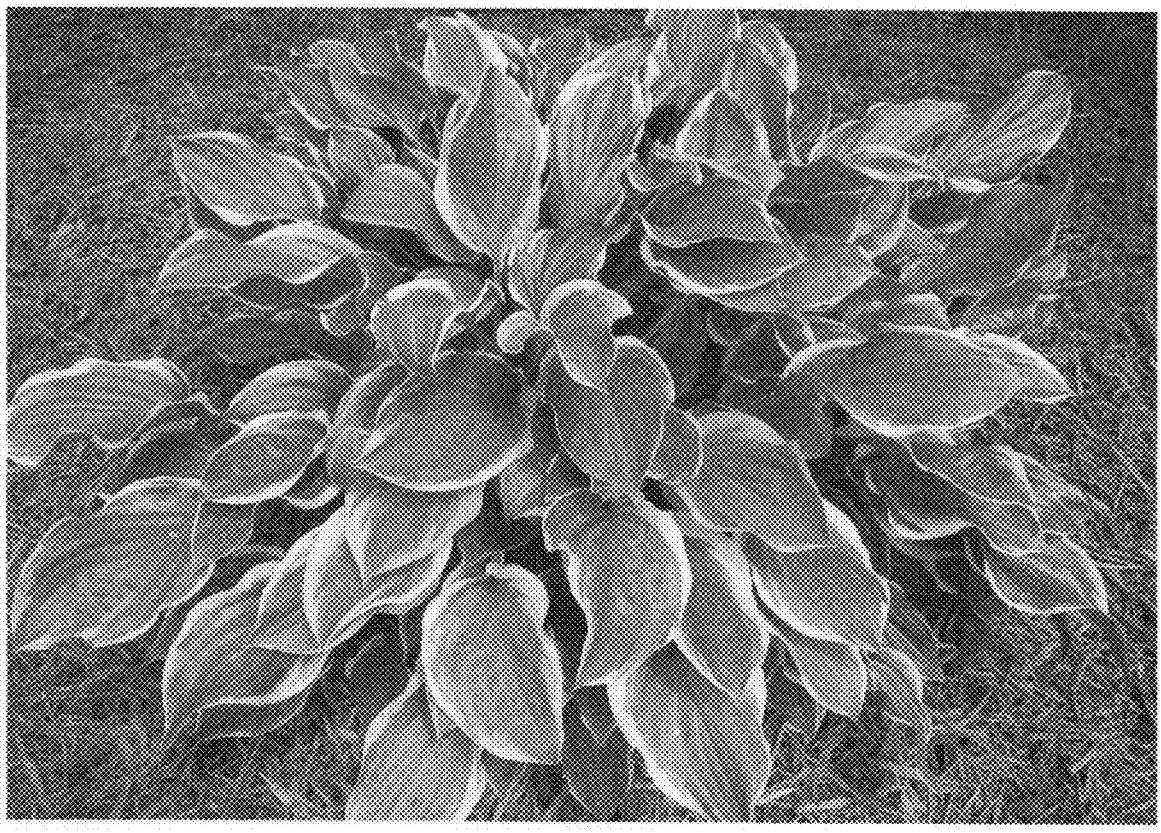

* * * * *